United States Patent [19]

Asdoorian et al.

[11] Patent Number: Plant 5,462

[45] Date of Patent: May 7, 1985

[54] NECTARINE TREE, ISLAND DELIGHT

[76] Inventors: Alan R. Asdoorian, 6384 Chico Ave.; Soren Asdoorian, 522 6th Ave., both of Kingsburg, Calif. 93631

[21] Appl. No.: 538,139

[22] Filed: Oct. 3, 1983

[51] Int. Cl.[3] ..... A01H 5/03

[52] U.S. Cl. ..... Plt./41

[58] Field of Search ..... Plt./41

*Primary Examiner*—Robert E. Bagwill

*Attorney, Agent, or Firm*—Huebner & Worrel

[57] ABSTRACT

A nectarine tree, generally similar to the Firebrite Nectarine Tree (unpatented), which it most nearly resembles, bearing large, yellow-fleshed fruit which ripens eight to ten days earlier than that of the Firebrite.

1 Drawing Figure

BACKGROUND OF THE VARIETY

The present invention relates to a new and distinct variety of nectarine tree which has been denominated by the varietal name "ISLAND DELIGHT" and which is broadly similar to the Firebrite Nectarine Tree (unpatented), of which it is believed to be a mutant, bearing large, highly-colored fruit having yellow flesh, but from which it differs in bearing fruit which ripens approximately eight to ten days earlier than that of the Firebrite variety.

The Firebrite variety of nectarine tree has become well known as a moderately vigorous, productive bearer of relatively large, ovate fruit having an attractive, bright red coloring and firm, flavorful yellow flesh. It has long been known that the purchase of fruit, such as nectarines, by consumers is often largely influenced by the fruit's size and exterior coloration. Thus, it has been recognized as desirable to provide a nectarine tree bearing fruit having the commercially asthetic appeal of fruits such as that of the Firebrite variety, but which ripens earlier than the varieties which it most nearly resembles, whereby the fruit can be brought to market at a time when competition is at a minimum.

ORIGIN AND ASEXUAL REPRODUCTION OF THE NEW VARIETY

The new variety of the nectarine tree was discovered by both of us in 1979 as a mutation growing in an orchard of unpatented Firebrite nectarine trees owned by Soren Asdoorian and located at 522 6th Avenue, in the City of Kingsburg, in the County of Fresno, in the State of California.

The mutation was asexually reproduced in 1979 by the late Lee Brand, formerly of Fresno, Calif., by budding scions of the new variety onto trees of the designated orchard under our supervision and control. The fruit and tree characteristics resulting from this budding have virtually continuously been observed by us and have proved to be identical to those of the original mutation.

SUMMARY OF THE NEW VARIETY

The instant variety of nectarine tree is broadly characterized by exhibiting characteristics generally resembling those of the Firebrite Nectarine Tree in its productive bearing of large, brightly-colored fruit having firm, yellow flesh, though distinguished therefrom as to novelty by the ripening of its fruit about eight to ten days earlier than that of the Firebrite variety.

The new nectarine tree bears fruit whose skin, over most of its surface area, is colored light red (Plate 4-L-10) to garnet (Plate 6-L-5), over a ground color of yellow (Plate 11-J-2), and which has a semi-freestone, an average axial diameter of 65.8 millimeters, and which ripens for commercial picking between June 8 and June 15.

BRIEF DESCRIPTION OF THE DRAWING

The accompanying drawing is a color photograph of four mature nectarines of the subject variety with one of the fruits divided along the suture plane to show the flesh color and stone characteristics, together with a representative twig bearing leaves characteristic of the new variety.

DETAILED DESCRIPTION

Referring more specifically to the pomological details of the new and distinct variety of nectarine tree, the following has been observed under the ecological conditions prevailing in the designated orchard in Fresno, County, Calif. All color code plate identifications are by reference to the Maerz and Paul *Dictionary of Color,* 1950 edition.

TREE

Size; Large.

Figure: Upright when young; spreading with cropping and maturity; form and density determined by pruning.

Vigor: Vigorous.

Productivity: Productive.

Regularity of bearing: Regular.

Trunk:

- *Thickness.*—Medium.
- *Surface texture.*—Medium.
- *Bark.*—Gray-brown (Plate 15-C-5); numerous lenticels.

Branches:

- *Size.*—Medium.
- *Surface texture.*—Medium.
- *Color.*—Mature, one-year old shoots: Light brown (Plate 13-G-7); young shoots; Green (Plate 17-I-5), with some red on exposed sides.

Leaves:

- *Size.*—Medium to large.

*Length.*—Average 17.1 cm.

*Width.*—Average 4.8 cm.

*Thickness.*—Average.

*Form.*—Lanceolate, tip accuminate and often twisted and curved to right or left.

*Color.*—Upper leaf surface: Dark green (Plate 24-J-7), lower leaf surface: Lighter green (Plate 21-F-4).

*Marginal form.*—Broadly crenate, tipped with small brown gland (Plate 15-A-11); margin gently undulates; leaf margins of mature leaves at times curling inward, especially apically; leaf blade usually slightly curved downward.

*Petiole.*—Size: medium; length: 9–13 mm.; thickness: 1.5 to 2 mm.; color: Green (Plate 19-H-3).

*Stem gland.*—Size: medium; shape: reniform; color: Green (Plate 19-K-5) when young, darkening and deteriorating with age; number: 3–6; commonly, 2–3 glands alternate in position on petiole, with 1–2 more on base of leaf margin.

*Stipules.*—Usually 2 at base of leaf petiole; length: 8–10 mm.; color — Green (Plate 19-I-6) when young becoming Brown (Plate 15-A-11) with age; early deciduous.

Buds:

*Size.*—Medium.

*Shape.*—Conic.

*Surface.*—Pubescent.

FRUIT

Maturity: Tree ripe to maturity — June 18; commerical maturity — June 8; most recent picking: first picking — June 8, 1983; last picking — June 15, 1983.

Size:

*Uniformity.*—Uniform size, large.

*Average diameter.*—Axial — 65.8 mm.; Suture — 65.7 mm.; Cheek — 66.7 mm.

Form:

*Symmetry.*—Slightly asymmetrical, with one half often larger; globose to slightly ovate in lateral aspect; nearly globose in apical aspect.

*Suture.*—Distinct, moderately deep groove extending from base to apex on ventral side; visible on dorsal side, although less pronounced, appearing as a shallow depression from apex to base; dorsal suture usually strongly depressed and extending approximately 10–12 mm., from just beyond the apex.

*Ventral surface.*—Rounded and moderately lipped, both sides along entire surface of the suture; lips usually unequal, with one side stronger than the other.

*Stem cavity.*—Small, shallow; depth — 8–10 mm.; width — 14–16 mm.; length — 19–23 mm.; axial aspect round to somewhat oblong, longer in suture plane; suture line usually visible on both dorsal and ventral sides, deeper on ventral side.

*Base.*—Rounded to slightly truncate; usually slightly oblique to fruit axis; shorter on ventral side.

*Stem.*—Moderate to short; length — 8–10 mm.; color — Light green (Plate 19-K-5).

*Apex.*—Rounded with pistil point apical and recessed in suture groove.

*Skin.*—Thickness — moderate; texture — medium. Peels free from flesh at soft-ripe maturity. Free of acidity when fully mature.

*Tendency to crack.*—No observed tendency.

*Color.*—Ground color — Yellow (Plate 11-J-2) at full maturity; blush — Light Red (Plate 4-L-10) to Garnet (Plate 6-L-5) on exposed surfaces; blush coloration commonly covering 60%–80% of fruit surface, more so over apical end. Numerous yellow dots appearing over surface of blushed areas, at times coalescing into russeted areas.

*Pubescence.*—None.

Flesh:

*Color.*—Yellow (Plate 9-K-4), free of red flecks; uniform and clear throughout.

*Color of pit cavity.*—Yellow (Plate 9-K-4); fibers — moderate, white.

*Amygdalin.*—Moderate to slight.

*Juice.*—Abundant when soft ripe.

*Flavor.*—Pronounced, good; slightly acid.

*Aroma.*—Distinct, good, above average.

*Texture.*—Firm, meaty.

*Fibers.*—Average in number, fine, tender.

*Ripening.*—More or less evenly, beginning at ventral surface.

*Eating quality.*—Good, above average.

Stone: Semi-free; adheres to flesh most strongly along dorsal and ventral edges; becomes more free with advanced maturity.

*Average size.*—Length — 36 mm.; width — 39 mm.; Thickness — 24 mm.

*Fibers.*—Short, white, few in number.

*Form.*—Lateral aspect slightly obovate; base rounded to slightly truncate.

*Base.*—Oblique to stone axis; shorter on ventral edge.

*Hilum.*—Small to medium in size; roughly oval; heavily eroded.

*Apex.*—Rounded; small and somewhat flattened tip.

*Sides.*—Somewhat variable but mostly nearly equal.

*Ridges.*—Numerous over axial shoulder in lateral aspect, usually substantially parallel to apical edge, down to midstone; deep grooves near apex with tops of ridges slightly eroded; some short and deep grooves over basal shoulder converging basally.

*Pits.*—Variable, circular to oblong.

*Ventral edge.*—Medium to wide with coalesced short wings convering apically; relatively smooth in outline.

*Dorsal edge.*—Medium in width with deep and moderately wide groove extending from base to apex; groove narrowing near apical end; dorsal shoulder slightly eroded.

*Color.*—Light Buff (Plate 11-B- 2).

*Tendency to split.*—Moderate, most commonly internally.

Use: Fresh market for both local and long distance shipping.

Keeping quality: Average.

Shipping quality: Average.

Resistance to insects and disease: No particular susceptibilities noted.

Although the new variety of nectarine tree possesses the decribed characteristics as a result of the growing conditions prevailing in Fresno County, Calif., in the central part of the San Joaquin Valley, it is to be understood that variations in the usual magnitude in characteristics incident to growing conditions, fertilization, pruning and pest control are to be expected.

Having thus described and illustrated our new variety of nectarine tree, what is new and desired to be secured by Letters Patent is:

1. A new and distinct variety of nectarine tree, substantially as illustrated and described, broadly characterized by its bearing of large, yellow-fleshed fruit and by its general resemblance to the unpatented Firebrite Nectarine Tree, of which it is believed to be a mutant, but from which it is distinguished as to novelty by its fruit ripening approximately eight to ten days earlier than the fruit of the Firebrite variety, and by its fruit having a skin covered over approximately 60% to 80% of its surface by a blush color ranging from light red to garnet on a ground color of yellow.

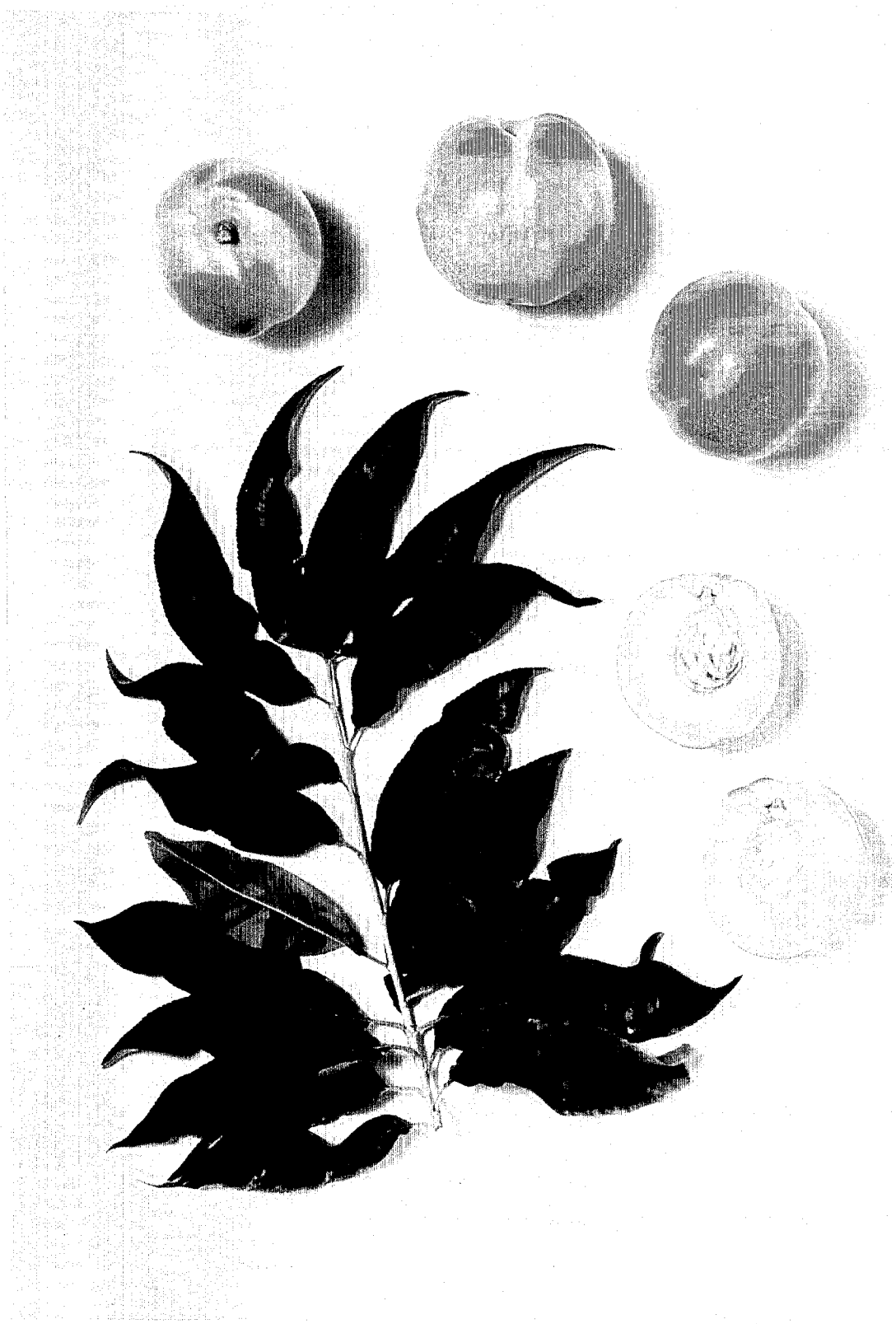

* * * * *